United States Patent [19]

Bullard

[11] Patent Number: 5,665,052

[45] Date of Patent: *Sep. 9, 1997

[54] MULTIFUNCTIONAL INTUBATING GUIDE STYLET AND LARYNGOSCOPE

[76] Inventor: James Roger Bullard, P.O. Box 14727, Augusta, Ga. 30909

[*] Notice: The term of this patent shall not extend beyond the expiration date of Pat. No. 5,551,946.

[21] Appl. No.: 645,442

[22] Filed: May 13, 1996

Related U.S. Application Data

[63] Continuation of Ser. No. 245,026, May 17, 1994, Pat. No. 5,551,946.

[51] Int. Cl.⁶ .................................................. A61B 1/267
[52] U.S. Cl. ........................... 600/194; 600/114; 600/120; 600/187; 600/188; 600/197; 600/199
[58] Field of Search ............................. 600/114, 120, 600/167, 188, 194, 197, 199; 128/207.14

[56] References Cited

U.S. PATENT DOCUMENTS

| | | | |
|---|---|---|---|
| 4,022,219 | 5/1977 | Basta | 128/351 |
| 4,086,919 | 5/1978 | Bullard | 128/11 |
| 4,565,187 | 1/1986 | Soloway | 128/11 |
| 4,742,819 | 5/1988 | George | 128/6 |
| 4,865,586 | 9/1989 | Hedberg | 604/93 |
| 4,905,669 | 3/1990 | Bullard et al. | 128/11 |
| 5,003,963 | 4/1991 | Bullard et al. | 128/11 |
| 5,058,577 | 10/1991 | Six | 128/200.26 |
| 5,060,633 | 10/1991 | Gibson | 128/11 |
| 5,095,888 | 3/1992 | Hawley | 128/10 |
| 5,174,283 | 12/1992 | Parker | 128/200.26 |
| 5,183,031 | 2/1993 | Rossoff | 128/6 |
| 5,193,533 | 3/1993 | Body et al. | 128/207.14 |
| 5,203,320 | 4/1993 | Augustine | 128/10 |
| 5,279,281 | 1/1994 | Harvey | 128/4 |
| 5,327,881 | 7/1994 | Greene | 128/11 |
| 5,368,579 | 11/1994 | Sandridge | 604/249 |
| 5,551,946 | 9/1996 | Bullard | 600/194 |

FOREIGN PATENT DOCUMENTS 0465942  1/1992  European Pat. Off.

OTHER PUBLICATIONS

Circon ACMI "Bullard Intubating Laryngoscopes".
Circon ACMI "Bullard™ Intubating Laryngoscopes".
"Circon ACMI Operating & Maintenance Manual Catalog No. LAR–P Pediatric, LAR–A Adult Bullard Intubating Laryngoscopes".
Circon ACMI "Introducing Stylets for Bullard™ Intubating Laryngoscopes"; Published 1991.
Sales Sheets, Bay Medical, Inc.

*Primary Examiner*—Beverly M. Flanagan
*Attorney, Agent, or Firm*—St. Onge Steward Johnston & Reens

[57] ABSTRACT

A multifunctional intubating stylet and laryngoscope, and a method of intubating a patient, comprise a laryngoscope body, and a hollow tubular intubating stylet affixed to and extending generally parallel to the laryngoscope body. An endotracheal tube is mounted on the exterior of the stylet. A guide member is passed through the interior of the stylet and advanced through the patient's vocal cords into the trachea. The endotracheal tube is then advanced along the guide member until it is established in a desired location in the patient's trachea to permit ventilation of the patient.

13 Claims, 4 Drawing Sheets

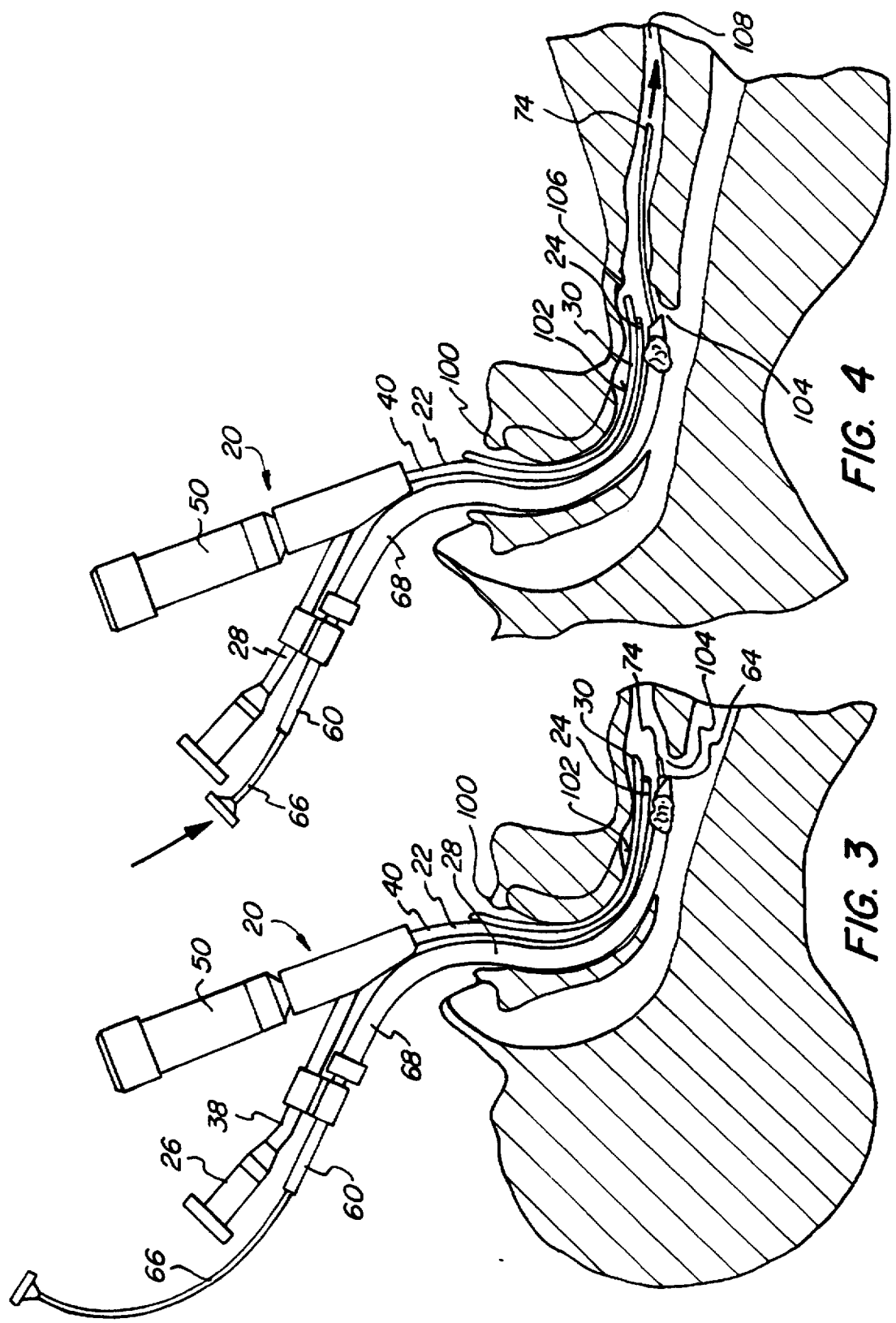

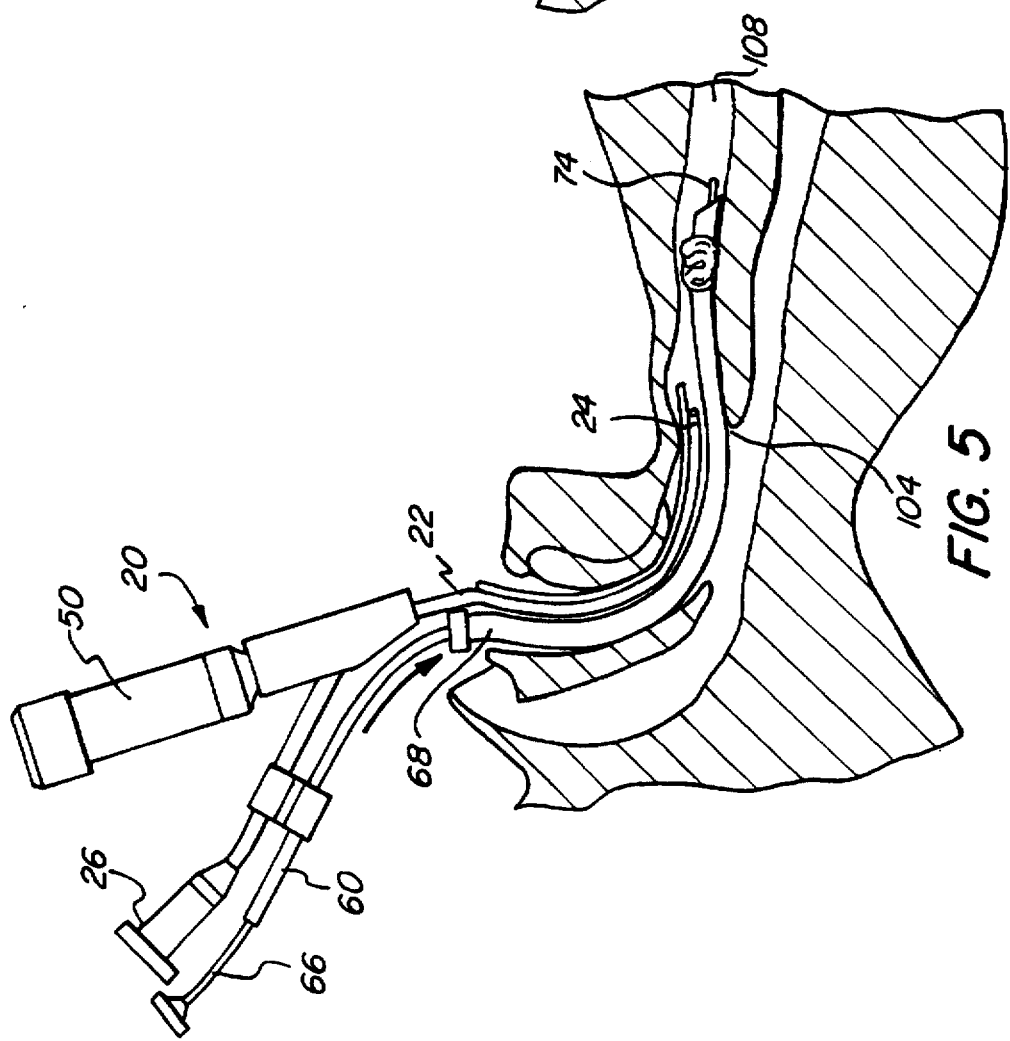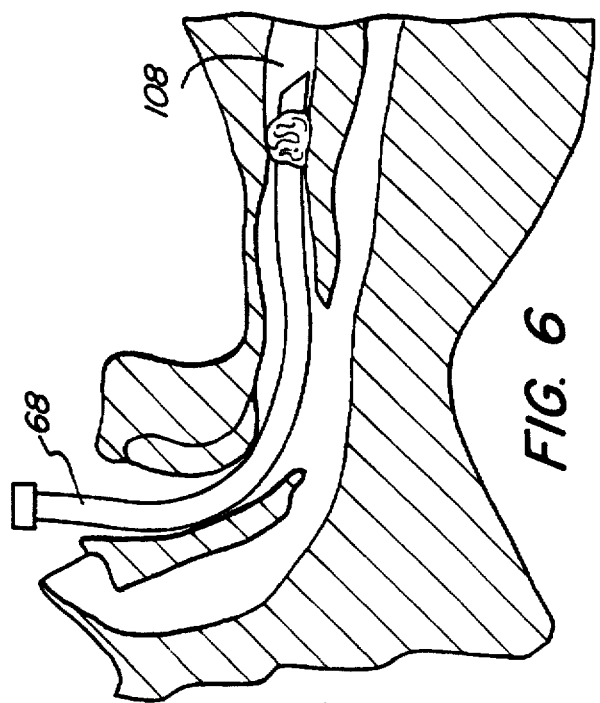

MULTIFUNCTIONAL INTUBATING GUIDE STYLET AND LARYNGOSCOPE

This application is a continuation of application Ser. No. 08/245,026 filed May 17, 1994 now U.S. Pat. No. 5,551,946.

FIELD OF THE INVENTION

The present invention relates to the field of medical optical devices permitting diagnosis and minimally invasive treatment and surgery, and more particularly, to an improved laryngoscope with a novel intubating guide stylet.

BACKGROUND OF THE INVENTION

Laryngoscopes are used to facilitate endotracheal intubation of a patient during surgery to provide a positive air passageway for the administration of anesthesia and/or for the mechanical ventilation of the lungs of the patient. In the human anatomy, the epiglottis normally overlies the glottic opening into the larynx to prevent the passage of food into the trachea during eating; therefore, in endotracheal intubation, it is necessary to displace the epiglottis from the glottic opening to permit the endotracheal air tube to be inserted into the trachea.

A laryngoscope having means for indirect illumination and visualization of the pharyngeal areas of the body is disclosed in my U.S. Pat. No. 4,086,919, the disclosure of which is hereby incorporated by reference. U.S. Pat. No. 4,086,919 discloses a laryngoscope (hereafter the "Bullard Laryngoscope") for endotracheal intubation which comprises a housing containing a working channel for containing forceps and channels containing fiber optics for lighting and viewing the internal areas of the body; and a laryngoscope blade for manipulating the epiglottis of a patient to enable viewing of a target area.

Various other laryngoscope constructions are known. Other prior art laryngoscopes have consisted of a metal blade which is supportably attached to a handle and is inserted through the mouth of the patient into the pharyngeal area to displace the tongue and epiglottis and permit direct visualization of the glottic opening through the mouth opening. Such laryngoscopes have been provided with a light source which is directed along the blade to illuminate the area beyond the distal end of the blade Two general types of rigid blade constructions are the straight, or so called "Miller blade", and the slightly curved, or so called "Macintosh blade". Curved laryngoscope blade constructions having light means to facilitate illumination of the areas of observation are described in U.S. Pat. Nos. 3,598,113; 3,643,654; 3,766,909; and 3,771,514. The Bullard Laryngoscope improves over these prior art laryngoscopes by providing an apparatus permitting the simple and rapid visualization of a target area such as the glottis to guide the insertion of an endotracheal tube.

The technique of intubation utilizing Bullard laryngoscopes is accomplished with a direct view of the larynx using either an intubating forceps or a solid stylet rod. The oral introduction and placement of the Bullard laryngoscope in a patient is described as follows, and is the same whether the intubating forceps or the solid stylet rod is used.

The blade of the Bullard laryngoscope is inserted into the oral cavity and the laryngoscope is rotated from the horizontal to the vertical position, allowing the anatomically shaped blade to slide around the tongue. Once the laryngoscope is fully vertical, final placement is facilitated by allowing the blade to drop momentarily to the posterior pharynx of the patient. The blade is then elevated against the tongue's dorsal surface. Only minimal upward movement exerted along the axis of the laryngoscope handle is required. This upward movement will result in the blade of the Bullard laryngoscope lifting the epiglottis, providing complete visualization of the glottic opening.

Prior to insertion of the Bullard laryngoscope into the patient, the user will have loaded an endotracheal tube onto the laryngoscope by using the jaws of the intubating forceps in the working channel of the Bullard laryngoscope to grasp a Murphy eye in the endotracheal tube. The tube is brought to the patient's laryngeal entrance together with the laryngoscope by the above steps. Thereafter, the endotracheal tube is advanced by advancing the forceps towards the vocal cords until the tube is past the vocal cords. At this point the forceps are released from the endotracheal tube and the tube may be advanced in the trachea to the extent necessary. Alternatively, the endotracheal tube may be fitted over a solid stylet rod that has an end located adjacent the viewing lens of the Bullard Laryngoscope, and, using the viewing capabilities of the laryngoscope, the endotracheal tube is pushed off the solid stylet rod while the laryngoscope is removed from the patient.

However, it has been found that even with the Bullard laryngoscope, if the endotracheal tube is not properly aimed or positioned by the doctor, that it will not pass between the vocal cords in the glottic opening, potentially causing trauma, or at the least, requiring more attempts at establishing the patient's airway.

It is to be appreciated teat multiple positioning and repositioning is time consuming and increases the risk of creating patient trauma and possible oxygen lack. The extra time required to replace a misplaced endotracheal tube translates into an increased operating room time and cost. It would be desirable to minimize risk by eliminating extra steps currently needed to establish an endotracheal tube as a patient's airway.

In more complex situations, i.e. where the patient's lungs are to be surveyed with a bronchoscope, or where a double lumen endotracheal tube is to be used, or where high frequency jet ventilation is needed to provide the patient with oxygen, the known Bullard laryngoscope and other known laryngoscopes do not provide a method of locating the bronchoscope and/or catheters at their desired locations. For example, with a flexible-directable bronchoscope, it is typically necessary to manually locate and feed the bronchoscope into the patient's trachea. It is to be appreciated that the bronchoscope is a delicate optical instrument that can be damaged if the patient is experiencing muscle spasms or if the doctor using the instrument does not correctly align the bronchoscope before advancing it past the vocal cords. A typical replacement cost for a damaged fiber optic cable of a flexible directable bronchoscope is at least $3000.

SUMMARY OF THE INVENTION

It is an object of the invention to provide a laryngoscope with a multifunctional hollow stylet to act as a support for an endotracheal tube, and which receives within it a guide member that can be easily manipulated and directed down the patient's larynx past the glottic opening between the vocal cords, so that the endotracheal tube can then be established using the guide member to quickly and accurately position the endotracheal tube.

These objects, and other objects as disclosed in this application, are achieved by a laryngoscope and a multifunctional intubating stylet as described below.

The laryngoscope comprises a body with a distal end and a proximal end. The body has both a means for viewing and a means for illuminating a field adjacent its distal end.

The multifunctional stylet is a hollow tubular stylet and is affixed to the body by a connection remote from the stylet's distal end. The stylet's distal end is adjacent to the body's distal end. The stylet is sized to permit the passage of a flexible guide member through its inner diameter. In use, an endotracheal tube is mounted on the exterior of the stylet prior to use With a patient. The stylet is preferably a rigid tube. The flexible guide member that is passed through the stylet preferably comprises a medical optical apparatus such as a flexible-directable bronchoscope; or a flexible hollow catheter.

A method of intubating a patient in accordance with the invention involves the use of the above described laryngoscope and intubating stylet, and comprises the steps of locating the laryngoscope and stylet in a patient's oral passageway; passing the flexible guide member through the stylet until its distal end is located at the end of the stylet; visualizing the patient's glottic opening using the viewing and illuminating means of the laryngoscope; advancing the flexible guide member between the patient's vocal cords and at least 5 centimeters beyond the glottic opening into the patient's trachea. The endotracheal tube is pushed off the stylet and advanced along the guide member until it is positioned to permit proper ventilation of the patient. The guide member and laryngoscope and stylet are then removed from the patient's mouth.

The method of the invention provides the benefits of visual certainty as to where the guide member and endotracheal tube are being located; it reduces trauma caused by the repetitive efforts to establish an endotracheal tube which were often required with prior art devices and methods. The present invention therefore provides a laryngoscope which provides substantial improvements in operational flexibility as compared with prior art devices.

Other objects, aspects and features of the present invention in addition to those mentioned above will be pointed out in detail or will be understood from the following detailed description provided in conjunction with the accompanying drawings.

BRIEF DESCRIPTION OF THE DRAWINGS

The foregoing aspects and other features of the invention are explained in the following description, taken in connection with the accompanying drawings, wherein:

FIGS. 3–6 are a series of schematic cross-sectional views showing the use of the intubating guide stylet and laryngoscope of the present invention in connection with the intubation of a patient.

DETAILED DESCRIPTION OF THE INVENTION

Figures 1, 2:
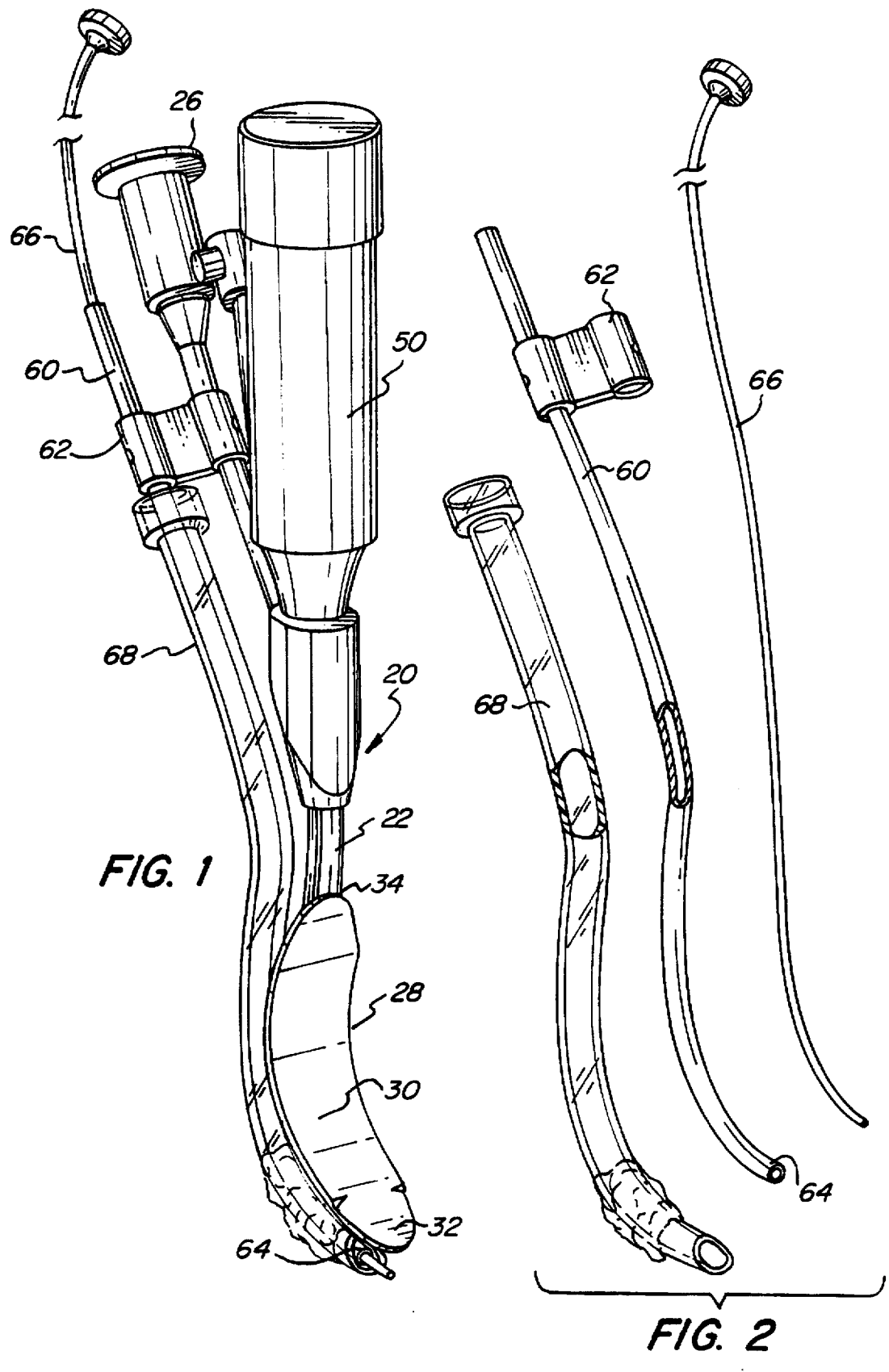
FIG. 1 is a perspective view of a multifunctional intubating guide stylet and laryngoscope in accordance with one embodiment of the invention.
FIG. 2 is an exploded view of the intubating guide stylet, guide member and endotracheal tube of FIG. 1.

Referring to FIGS. 1–6, where like numbered elements in the drawings represent the same elements, a laryngoscope 20 is shown.

Laryngoscope 20 has a body 22 and is provided with a plurality of channels therein which extend from a distal end 24 to a proximal end 26 of the laryngoscope 20. Laryngoscope 20 is for use in an adult patient, and is curved at its lower section 28 to generally conform with the curvature of the normal human oral and pharyngeal passageways at about a ninety degree angle, preferably within a range of about 80–100 degrees. In a pediatric laryngoscope, the lower section 28 will be curved through a ninety degree angle though with a much smaller radius of curvature than the adult laryngoscope.

The blade 30 of the laryngoscope 20 generally comprises an elongate, rigid leaf or petal. The blade 30 in this embodiment has a distal end 32 intended for leading insertion into the patient's mouth and a proximal end 34 connected to the body 22. The blade 30 in the adult embodiment preferably has an anatomically curved configuration (as does body 22) with a distal end 32 such that a physician can insert the blade 30 into the mouth of a patient while the patient is in a supine position. However, the invention is also usable in laryngoscopes with straight bodies and blades as are preferred in pediatric laryngoscopes as described above. At least one working channel for forceps and other instruments will also be provided in body 22.

Optical channel 38 is provided with a flexible optical image transmitting medium, which is preferably a bundle of optic fibers which extend from the distal end 24 to the proximal end 26 of the laryngoscope 20. The optical image transmitting medium in the optical channel 38 permits optical images to be transmitted through the optical channel 38. A viewing lens on the distal end of the optical channel 38 collects optical images for transmission through the optical channel 38. The laryngoscope 20 is preferably adapted so that a video camera may be operably coupled to the proximal end 26 of the laryngoscope 20 at the proximal end of the optical channel 38 to receive and transmit the optical images from the optical channel 38 to a television monitor (not shown) and to a video recording apparatus such as a video cassette recorder (not shown). Light channel 40 is provided with the light transmitting medium that permits light to be transmitted through the light channel 40. This permits the illumination of the field where treatment, diagnosis or operations are desired. The light transmitting medium is preferably a plurality of optic fibers with another suitable lens at the distal end thereof as necessary. The light transmitting medium is connected at its proximal end to a light source of a sufficiently high intensity to permit visualization of the field. The light source may for example comprise a halogen bulb located in battery handle 50.

The multifunctional stylet 60 is a hollow tube, preferably fabricated from a rigid material such as stainless steel. Stylet 60 is affixed to the body 22 by a connection 62 remote from the stylet's distal end 64. The stylet's distal end 64 is adjacent to the body's distal end 24. The stylet 60 is sized to permit the passage of a flexible guide member 66 through its inner diameter. In use, an endotracheal tube 68 is mounted on the exterior of the stylet 60. Endotracheal tube 68 may be a single lumen or a double lumen tube.

The flexible guide member 66 that is passed through the stylet 60 may comprise a medical optical apparatus such as a bronchoscope, or it may be a flexible hollow catheter, or even, in some instances, a solid flexible rod. If flexible guide member 66 is a catheter, it may be used to deliver an anesthetic to laryngeal and subglottic areas. In alternative embodiments, the catheter may serve as a conduit for high frequency jet ventilation of the patient's lungs; or as a suctioning catheter; or a bronchial blocker, i.e. an inflatable collar might be affixed to the end of the catheter and inflated when the catheter is positioned in the right or left main stem bronchus, thus blocking off one lung from the other.

Figure 7:
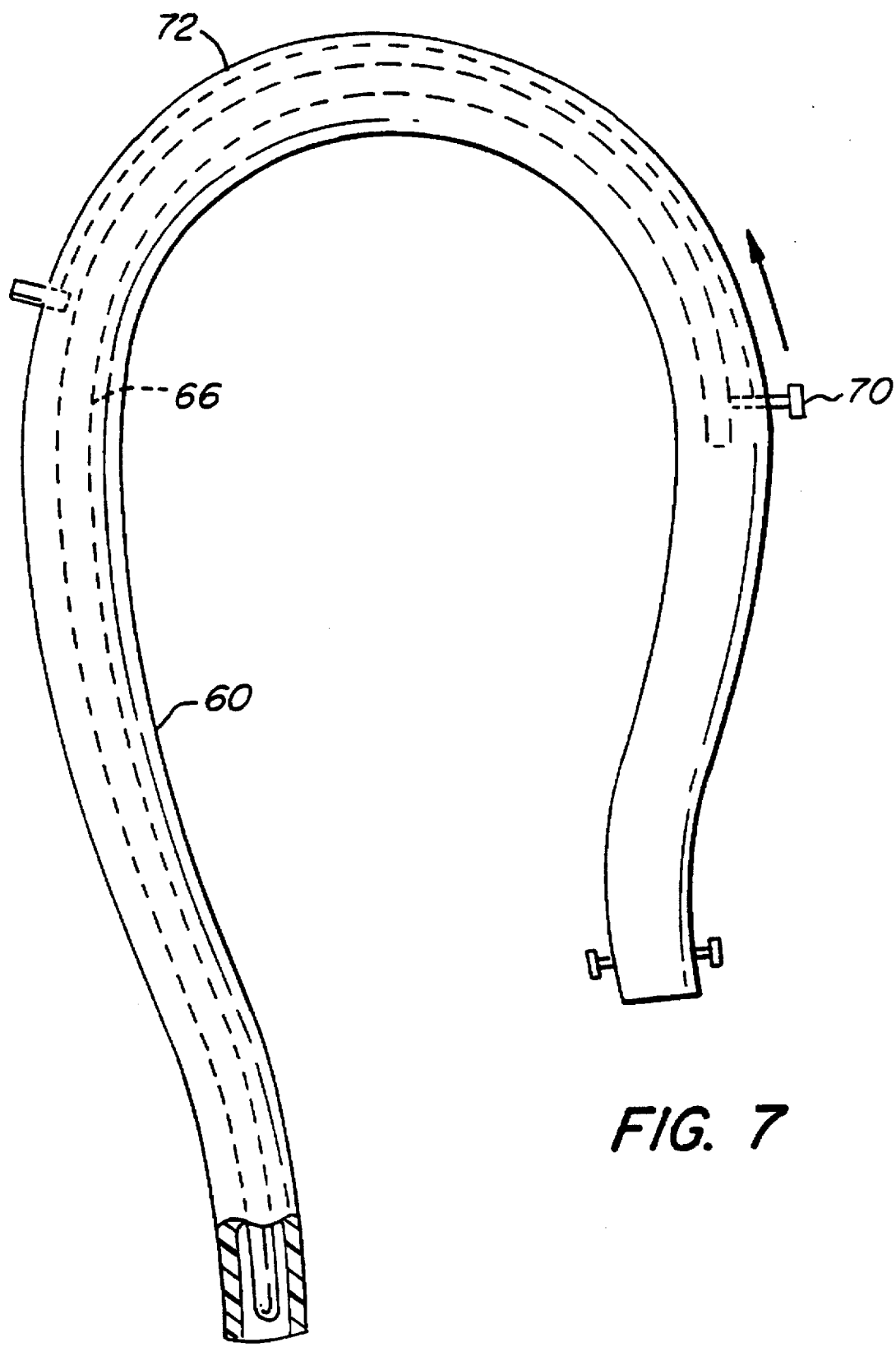
FIG. 7 is a cross-sectional view of a portion of another embodiment of the intubating guide stylet of the invention.

In another embodiment shown in FIG. 7, the flexible guide member 66 is provided with a control tab 70 extending laterally from a longitudinal axis of the guide member 66. In such case, the stylet 60 will be provided with a longitudinal slot 72, and the tab 70 will extend from the guide member 66 through slot 72 to be manually operable to extend the guide member 66 from the distal end 64 of stylet 60 by moving tab 70 along slot 72 towards the stylet's distal end 64.

Referring to FIGS. 3–6, there is shown an illustrated view of a patient in the supine position with a laryngoscope 20 inserted into the patient's mouth 100 and showing the use of intubating stylet 60. A method of intubating a patient is illustrated in FIGS. 3–6. The initial step of the method is shown in FIG. 3, and comprises the step of locating the laryngoscope 20 and stylet 60 in a patient's oral passageway 102. The flexible guide member 66 may be passed through the stylet 60 prior to the placement of the laryngoscope 20 in the patient's airway, or it may be inserted inside the stylet 60 after the laryngoscope 20 is placed in the patient's airway. When the distal end 74 of the guide member 66 is located at the distal end 64 of the stylet 60, the patient's glottic opening 104 is visualized using the light and optical channels 40, 38 of the laryngoscope 20. As shown in FIG. 4, the flexible guide member 66 is then advanced between the patient's vocal cords 106 and at least 5 centimeters beyond the glottic opening into the patient's trachea 108. Referring now to FIG. 5, the endotracheal tube 68 is manually pushed off the stylet 60 and advanced along the guide member 66 until it is properly positioned to permit ventilation of the patient. As shown in FIG. 6, the guide member 66 and laryngoscope 20 may then be removed from the patient's mouth; the endotracheal tube 68 may then be connected to a source of oxygen to ventilate the patient or it may be connected to a source of anesthetic or therapeutic gases.

In one preferred embodiment of the method, the flexible guide member 66 comprises a flexible directable medical optical apparatus such as a bronchoscope. In this case the medical optical apparatus is advanced to at least the location of the patient's mid-trachea during the step of advancing said guide member 66 prior to establishing the endotracheal tube 68. The medical optical apparatus may also be advanced into the patient's lung cavities to permit inspection of the lungs. The use of the multifunctional stylet 60 in the method permits rapid and accurate placement of a bronchoscope, which can be a crucial life-saving element when there is an urgent need to remove a blocking foreign body in the patient's trachea.

In another preferred embodiment of the invention, the flexible guide member 66 may comprise a flexible hollow catheter. A liquid surface anesthetic may be injected through such a catheter to spray and anesthetize laryngeal and subglottic area of the patient prior to establishing the endotracheal tube. The catheter may be used for high frequency jet ventilation to the patient's lungs. The catheter may also be used to provide suction to a proximal end of the catheter to suction secretions from the patient. The intubating guide stylet thus provides a flexible method of locating such a catheter and to perform the above procedures without the additional step of manually locating such a catheter, because it is already located when the patient is intubated. The catheter may be left in place in the endotracheal tube and sealed with a luer lock, so that it is available for use as needed.

The method provides the benefits of visual certainty as to where the guide member 66 and endotracheal tube 68 are being located; it reduces trauma caused by the repetitive efforts to establish an endotracheal tube 68 which were often required with prior art devices and methods. The present invention permits effective use of the laryngoscope 20 in a variety of physical structures, by permitting the physician greater control of the placement of the endotracheal tube. It is to be appreciated that the present invention can be used with conventional Miller and Macintosh type laryngoscopes, including present and future variants thereof, as well as Bullard laryngoscopes, as shown in the preferred embodiments.

The present invention provides an important and timely contribution to the art of medical devices, by providing a laryngoscope that has better operational flexibility than any device known in the art.

It is to be appreciated that the foregoing is illustrative and not limiting of the invention, and that various changes and modifications to the preferred embodiments described above will be apparent to those skilled in the art. For example, the invention has application in other medical optical devices such as endoscopes, including arthroscopes and urethroscopes. Such changes and modifications can be made without departing from the spirit and scope of the present invention, and it is therefore intended that such changes and modifications be covered by the following claims.

What is claimed is:

1. An intubating guide stylet and laryngoscope, comprising:

a rigid curved body, having a distal end for fitting into human oral and pharyngeal passageways, said body containing therein both a means for viewing and a means for illuminating a field adjacent said distal end of said body, and a laryngoscope blade affixed to said distal end of said body;

a hollow tubular stylet having a distal end and a proximal end, said stylet being affixed to said body by a connection remote from said stylet distal end, said hollow stylet having an inner diameter adapted to permit a flexible guide member having a distal end to be passed therethrough, and an outer diameter adapted to permit an endotracheal tube to be mounted on the exterior of said stylet; said stylet distal end being located adjacent said distal end of said body such that, upon passage of a flexible guide member through said stylet, the flexible guide member will be manipulated to position the guide member at a desired position in a patient's anatomy with direct vision by said illuminating and viewing means of said body, such that an endotracheal tube, when mounted to said stylet, may be advanced along the stylet onto the guide member to be positioned in the patient at the desired position in the patient's anatomy.

2. An intubating guide stylet and laryngoscope in accordance with claim 1, wherein a flexible guide member is provided inside of said tublar stylet.

3. An intubating guide stylet and laryngoscope in accordance with claim 1, wherein said flexible guide member comprises a medical optical apparatus.

4. An intubating guide stylet and laryngoscope in accordance with claim 1, wherein a flexible guide member comprises a flexible hollow catheter.

5. An intubating guide stylet and laryngoscope in accordance with claim 4, wherein said flexible hollow catheter comprises a catheter selected from the group consisting of an anesthetic delivery catheter; a high frequency jet ventilation catheter; a suctioning catheter; and a bronchial blocking catheter.

6. An intubating guide stylet and laryngoscope in accordance with claim 2, wherein said flexible guide member is provided with a control tab extending laterally from a longitudinal axis of said guide member, and wherein said stylet is provided with a longitudinal slot, said tab extending from said guide member through said slot to be manually operable to extend said guide member from said distal end of said stylet by moving said tab along said slot towards said distal end of said stylet.

7. An intubating guide stylet and laryngoscope in accordance with claim 2, further comprising an endotracheal tube fitted onto said stylet.

8. An intubating guide stylet and laryngoscope in accordance with claim 7, wherein said endotracheal tube comprises a double lumen endotracheal tube.

9. An intubating guide stylet and laryngoscope in accordance with claim 1, wherein said stylet is rigid.

10. A medical optical device comprising:
- a rigid body having a distal end and a fiber optic optical channel for viewing a target area, and a fiber optic illuminating channel for providing light to the target area;
- a hollow tubular stylet having a distal end and a proximal end, said stylet being affixed to said body by a connection remote from said stylet distal end, said hollow stylet having an inner diameter sized to permit a flexible member to be passed therethrough, and an outer diameter sized to permit a flexible tube to be mounted on the exterior of said stylet; said stylet distal end being located adjacent said distal end of said body such that, upon passage of a flexible guide member through said stylet, the flexible guide member will be manipulated to position the guide member at a desired position in a patient's anatomy with direct vision by said illuminating and viewing means of said body, such that a flexible tube, when mounted to said stylet, may be advanced along the stylet onto the guide member to be positioned in the patient at the desired position in the patient's anatomy.

11. A medical optical device in accordance with claim 10, wherein a flexible guide member is provided inside of said tubular stylet.

12. A medical optical device in accordance with claim 11, wherein said flexible guide member comprises a flexible medical optical apparatus or a flexible hollow catheter.

13. A medical optical device in accordance with claim 11, further comprising a flexible ventilating tube fitted onto said stylet.

* * * * *